US012678112B2

(12) United States Patent
Ishida et al.

(10) Patent No.: US 12,678,112 B2
(45) Date of Patent: Jul. 14, 2026

(54) X-RAY IMAGE DIAGNOSTIC SYSTEM, X-RAY IMAGE DIAGNOSTIC METHOD, AND STORAGE MEDIUM

(71) Applicant: Canon Kabushiki Kaisha, Tokyo (JP)

(72) Inventors: Akihiro Ishida, Nasushiobara (JP); Takayuki Yamazaki, Nasushiobara (JP)

(73) Assignee: Canon Kabushiki Kaisha, Tokyo (JP)

( * ) Notice: Subject to any disclaimer, the term of this patent is extended or adjusted under 35 U.S.C. 154(b) by 151 days.

(21) Appl. No.: 18/751,208

(22) Filed: Jun. 22, 2024

(65) Prior Publication Data

US 2024/0423564 A1 Dec. 26, 2024

(30) Foreign Application Priority Data

Jun. 26, 2023 (JP) ................................. 2023-104052

(51) Int. Cl.
*A61B 6/42* (2024.01)
*A61B 6/00* (2006.01)

(52) U.S. Cl.
CPC .......... *A61B 6/4291* (2013.01); *A61B 6/4241* (2013.01); *A61B 6/488* (2013.01); *A61B 6/5205* (2013.01)

(58) Field of Classification Search
None
See application file for complete search history.

(56) References Cited

U.S. PATENT DOCUMENTS

| | | | | |
|---|---|---|---|---|
| 5,606,587 A | * | 2/1997 | Barski ...................... | G06T 7/11 378/62 |
| 9,134,434 B2 | * | 9/2015 | Niederlohner ......... | G21K 1/025 |
| 2019/0290235 A1 | * | 9/2019 | Tsuji .................... | A61B 6/5217 |

FOREIGN PATENT DOCUMENTS

JP 2011-229605 A 11/2011

* cited by examiner

*Primary Examiner* — Marcus H Taningco
(74) *Attorney, Agent, or Firm* — Oblon, McClelland, Maier & Neustadt, L.L.P.

(57) ABSTRACT

An X-ray image diagnostic system of an embodiment includes processing circuitry. The processing circuitry is configured to acquire an image obtained by imaging a plurality of detection elements that output signals in response to incident X-rays, and a plurality of scattered radiation removal plates arranged at least in a channel direction on the side of a first surface of the plurality of detection elements on which the X-rays are incident in a direction substantially normal to the first surface, and generate data regarding an irradiated area of each of the plurality of detection elements on the basis of the image.

10 Claims, 8 Drawing Sheets

153-1    153-2    153-3

ASG 151-7    151-8    151-9

ASG    151-4    151-5    151-6    ASG 151-1    151-2    151-3

C 153-4

ASG

FIG. 5

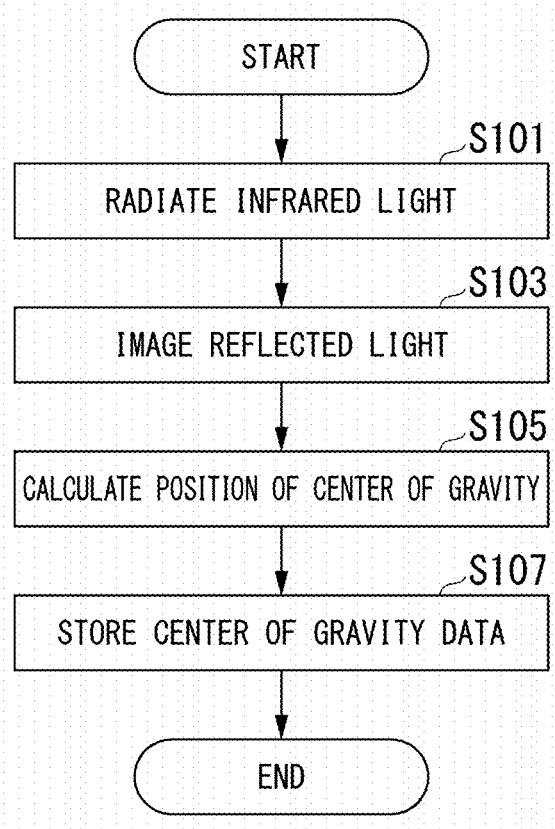

```
        ┌──────────────┐
        │    START     │
        └──────────────┘
                │
                ▼               S101
    ┌──────────────────────────┐
    │   RADIATE INFRARED LIGHT │
    └──────────────────────────┘
                │
                ▼               S103
    ┌──────────────────────────┐
    │   IMAGE REFLECTED LIGHT  │
    └──────────────────────────┘
                │
                ▼               S105
┌──────────────────────────────────┐
│ CALCULATE POSITION OF CENTER OF GRAVITY │
└──────────────────────────────────┘
                │
                ▼               S107
    ┌──────────────────────────┐
    │ STORE CENTER OF GRAVITY DATA │
    └──────────────────────────┘
                │
                ▼
        ┌──────────────┐
        │     END      │
        └──────────────┘
```

FIG. 6

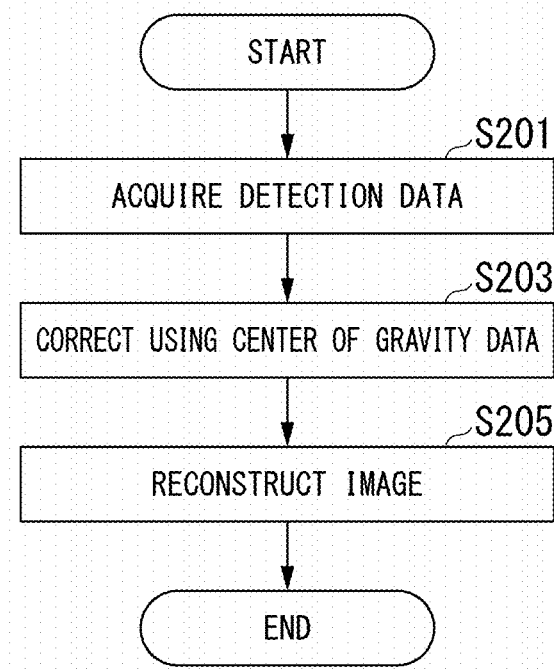

```
        ┌──────────────┐
        │    START     │
        └──────────────┘
                │
                ▼               S201
    ┌──────────────────────────┐
    │   ACQUIRE DETECTION DATA │
    └──────────────────────────┘
                │
                ▼               S203
    ┌──────────────────────────┐
    │ CORRECT USING CENTER OF GRAVITY DATA │
    └──────────────────────────┘
                │
                ▼               S205
    ┌──────────────────────────┐
    │     RECONSTRUCT IMAGE    │
    └──────────────────────────┘
                │
                ▼
        ┌──────────────┐
        │     END      │
        └──────────────┘
```

FIG. 7
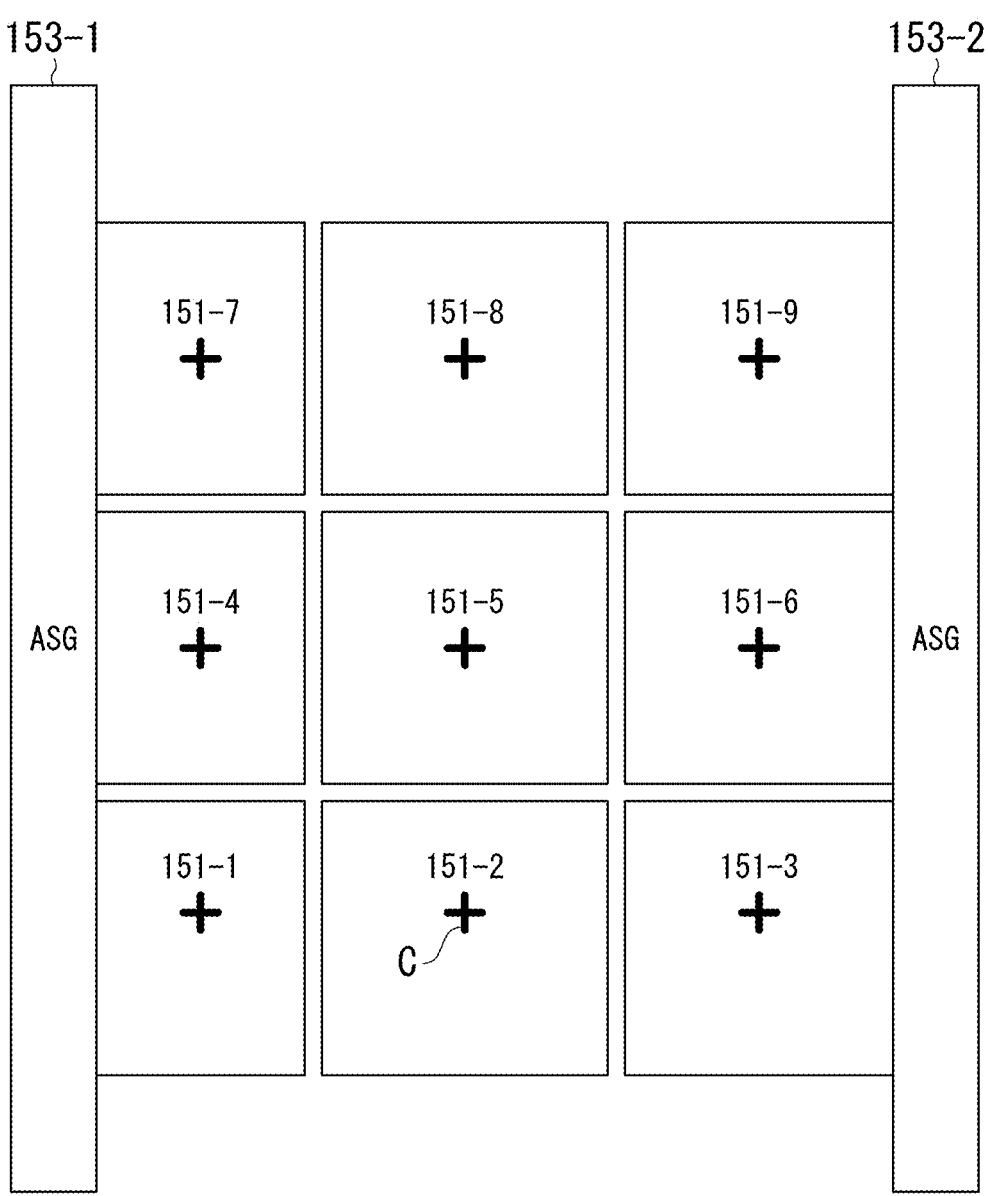
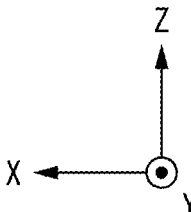

X-RAY IMAGE DIAGNOSTIC SYSTEM, X-RAY IMAGE DIAGNOSTIC METHOD, AND STORAGE MEDIUM

CROSS-REFERENCE TO RELATED APPLICATION

The present application claims priority based on Japanese Patent Application No. 2023-104052 filed Jun. 26, 2023, the content of which is incorporated herein by reference.

FIELD

Embodiments disclosed in this specification and drawings relate to an X-ray image diagnostic system, an X-ray image diagnostic method, and a storage medium.

BACKGROUND

In an X-ray computed tomography (CT) apparatus, a signal that depends on an X-ray flux is back-projected onto the position of the center of gravity of a range irradiated with X-rays in detection elements disposed in a planar manner within an X-ray detector to reconstruct an X-ray image. In direct conversion type X-ray detectors used in photon counting computed tomography (CT) apparatuses and the like, detection elements can be made smaller than those in conventional indirect conversion type X-ray detectors by making an electrode etching pattern finer.

A scattered radiation removal plate such as an anti-scatter-grid (ASG) used in X-ray detectors is limited by manufacturing technology and thus has not been made as fine as an electrode pattern generated by etching. For this reason, there is a possibility of misalignment in the positional relationship between the scattered radiation removal plate and electrodes (detection elements), which may cause a problem in the image quality of a reconstructed X-ray image. In particular, in the case of a configuration in which a plurality of detection elements are disposed in one grid of the scattered radiation removal plate, the influence of this misalignment increases. In addition, in the conventional method, irradiated positions are uniquely defined at equal intervals with the scattered radiation removal plate as a reference, but when a plurality of detection elements are disposed in one grid, the actual irradiated positions are not provided at equal intervals, which may cause a problem in the image quality of a reconstructed X-ray image.

BRIEF DESCRIPTION OF THE DRAWINGS

FIG. 5 is a flowchart showing an example of processing of calculating a position of the center of gravity of a detection element in the X-ray CT apparatus according to the first embodiment.

FIG. 6 is a flowchart showing an example of processing of reconstructing a CT image in the X-ray CT apparatus according to the first embodiment.

FIG. 7 is a diagram showing another example of a detection element image generated on the basis of infrared light (reflected light) in the first embodiment.

DETAILED DESCRIPTION

Hereinafter, an X-ray image diagnostic system, an X-ray image diagnostic method, and a storage medium according to embodiments will be described with reference to the drawings.

An X-ray image diagnostic system of an embodiment includes processing circuitry. The processing circuitry is configured to acquire an image obtained by imaging a plurality of detection elements that output signals in response to incident X-rays, and a plurality of scattered radiation removal plates arranged at least in a channel direction on the side of a first surface of the plurality of detection elements on which the X-rays are incident in a direction substantially normal to the first surface, and generate data regarding an irradiated area of each of the plurality of detection elements on the basis of the image.

First Embodiment

An X-ray image diagnostic system of a first embodiment includes an X-ray diagnostic apparatus that generates an X-ray image of the inside of a subject by detecting X-rays that have passed through the subject using an X-ray detector. In the X-ray image diagnostic system, the quality of the generated X-ray image can be improved by accurately ascertaining a range actually irradiated with X-rays (irradiated area) for each detection element included in the X-ray detector and performing projection processing on the basis of the position of the center of gravity of this range. Examples of the X-ray diagnostic apparatus include an X-ray CT apparatus, an X-ray diagnostic apparatus using a flat panel detector (FPD), and the like. Examples of the X-ray CT apparatus include a photon counting CT apparatus using a direct conversion type X-ray detector, an X-ray CT apparatus using an indirect conversion type X-ray detector, and the like. As an example, an X-ray CT apparatus (photon counting CT apparatus) will be described below.

[Configuration of X-Ray CT Apparatus]

Figure 1:
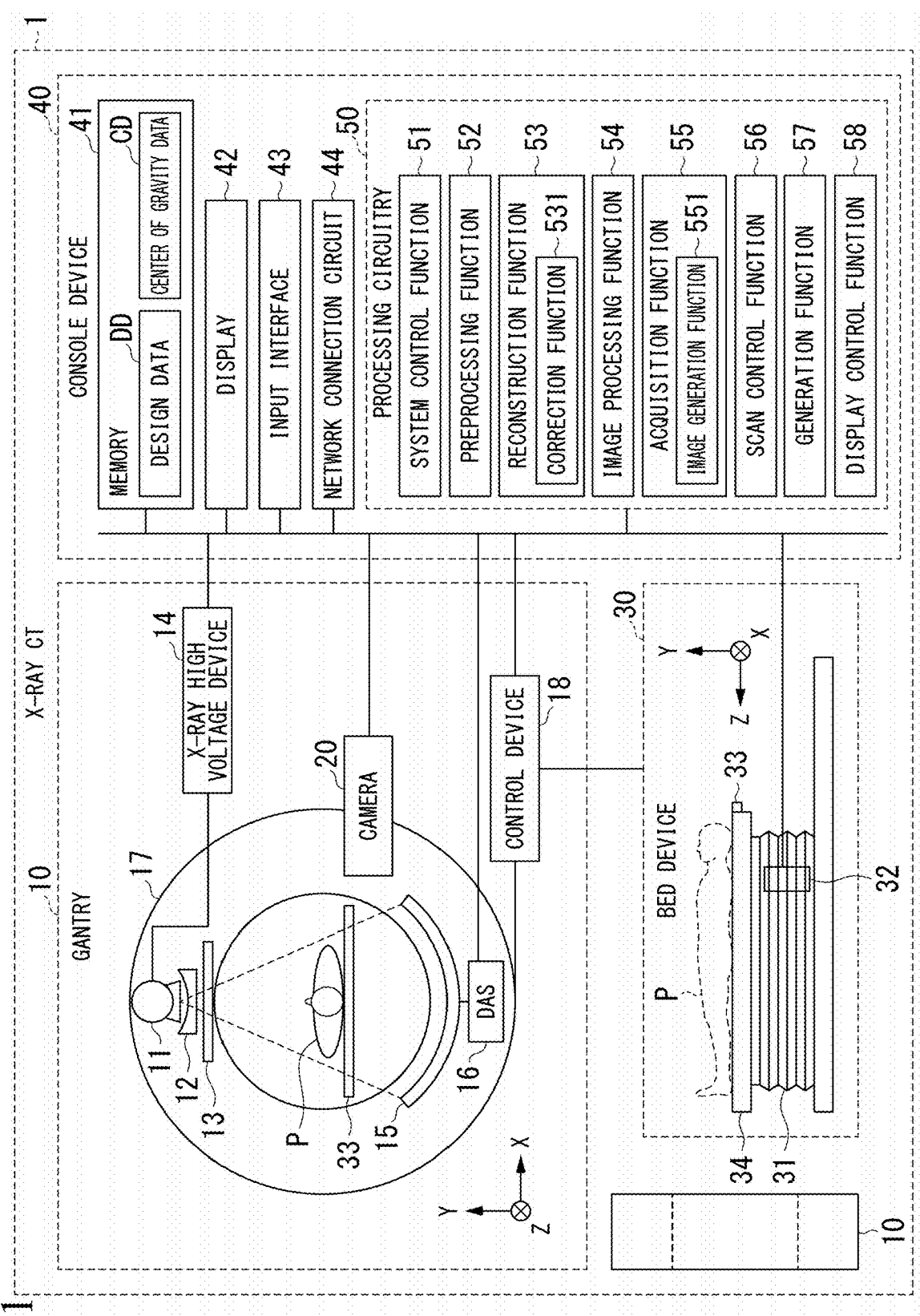
FIG. 1 is a diagram showing an example of a configuration of an X-ray CT apparatus according to a first embodiment.

FIG. 1 is a diagram showing an example of a configuration of an X-ray CT apparatus 1 (photon counting CT apparatus) according to the first embodiment. The X-ray CT apparatus 1 includes, for example, a gantry 10, a bed device 30, and a console device 40. Although FIG. 1 shows both a view of the gantry 10 in the Z-axis direction and a view in the X-axis direction for convenience of description, there is only one gantry 10 in reality. In the first embodiment, a rotation axis of a rotary frame 17 in a non-tilting state or the longitudinal direction of a top plate 33 of the bed device 30 is defined as the Z-axis direction, an axis orthogonal to the Z-axis direction and horizontal to the floor surface is defined as the X-axis direction, and a direction orthogonal to the Z-axis direction and perpendicular to the floor surface is defined as the Y-axis direction.

The gantry 10 includes, for example, an X-ray tube 11, a wedge 12, a collimator 13, an X-ray high voltage device 14, an X-ray detector 15, a data acquisition system (hereinafter referred to as DAS) 16, a rotary frame 17, a control device 18, and a camera 20.

The X-ray tube 11 generates X-rays by radiating thermo-electrons from a cathode (filament) toward an anode (target) by applying a high voltage from the X-ray high voltage device 14. The X-ray tube 11 includes a vacuum tube. For example, the X-ray tube 11 is a rotating anode type X-ray tube that generates X-rays by radiating thermoelectrons to a rotating anode.

The wedge 12 is a filter for adjusting the amount of X-rays radiated from the X-ray tube 11 to a subject P. The wedge 12 attenuates X-rays that pass through the wedge 12 such that the distribution of the amount of X-rays radiated from the X-ray tube 11 to the subject P becomes a predetermined distribution. The wedge 12 is also called a wedge filter or a bow-tie filter. The wedge 12 is, for example, made of aluminum processed to have a predetermined target angle and a predetermined thickness.

The collimator 13 is a mechanism for narrowing down a radiation range of X-rays that have passed through the wedge 12. The collimator 13 narrows down the radiation range of X-rays by forming a slit using a combination of a plurality of lead plates, for example. The collimator 13 may be called an X-ray diaphragm. A narrowing range of the collimator 13 may be mechanically driven.

The X-ray high voltage device 14 includes, for example, a high voltage generation device that is not shown and an X-ray control device that is not shown. The high voltage generation device has an electric circuit including a trans-former, a rectifier, and the like and generates a high voltage to be applied to the X-ray tube 11. The X-ray control device controls the output voltage of the high voltage generation device depending on the amount of X-rays to be generated in the X-ray tube 11. The high voltage generation device may boost a voltage using the aforementioned transformer or using an inverter. The X-ray high voltage device 14 may be provided on the rotary frame 17 or may be provided on the side of a fixed frame (not shown) of the gantry 10.

The X-ray detector 15 detects the intensity of X-rays that enter after being generated by the X-ray tube 11 and passing through the subject P. The X-ray detector 15 outputs an electrical signal (an optical signal or the like) corresponding to the detected intensity of X-rays to the DAS 16. The X-ray detector 15 has, for example, a plurality of detection element rows. Each of the plurality of detection element rows has a plurality of detection elements arranged in a channel direc-tion along an arc having the focal point of the X-ray tube 11 as a center. The plurality of detection element rows are arranged in a slice direction (row direction).

The X-ray detector 15 is, for example, a direct detection type detector. As the X-ray detector 15, for example, a semiconductor diode having electrodes attached to both ends of a semiconductor is applicable. X-ray photons incident on a semiconductor are converted into electron-hole pairs. The number of electron-hole pairs generated according to inci-dence of one X-ray photon depends on the energy of the incident X-ray photon. Electrons and holes are attracted to a pair of electrodes formed at both ends of the semiconduc-tor. The pair of electrodes generate electric pulses having peak values depending on the charge of electron-hole pairs. One electric pulse has a peak value that corresponds to the energy of the incident X-ray photon.

Figure 2A:
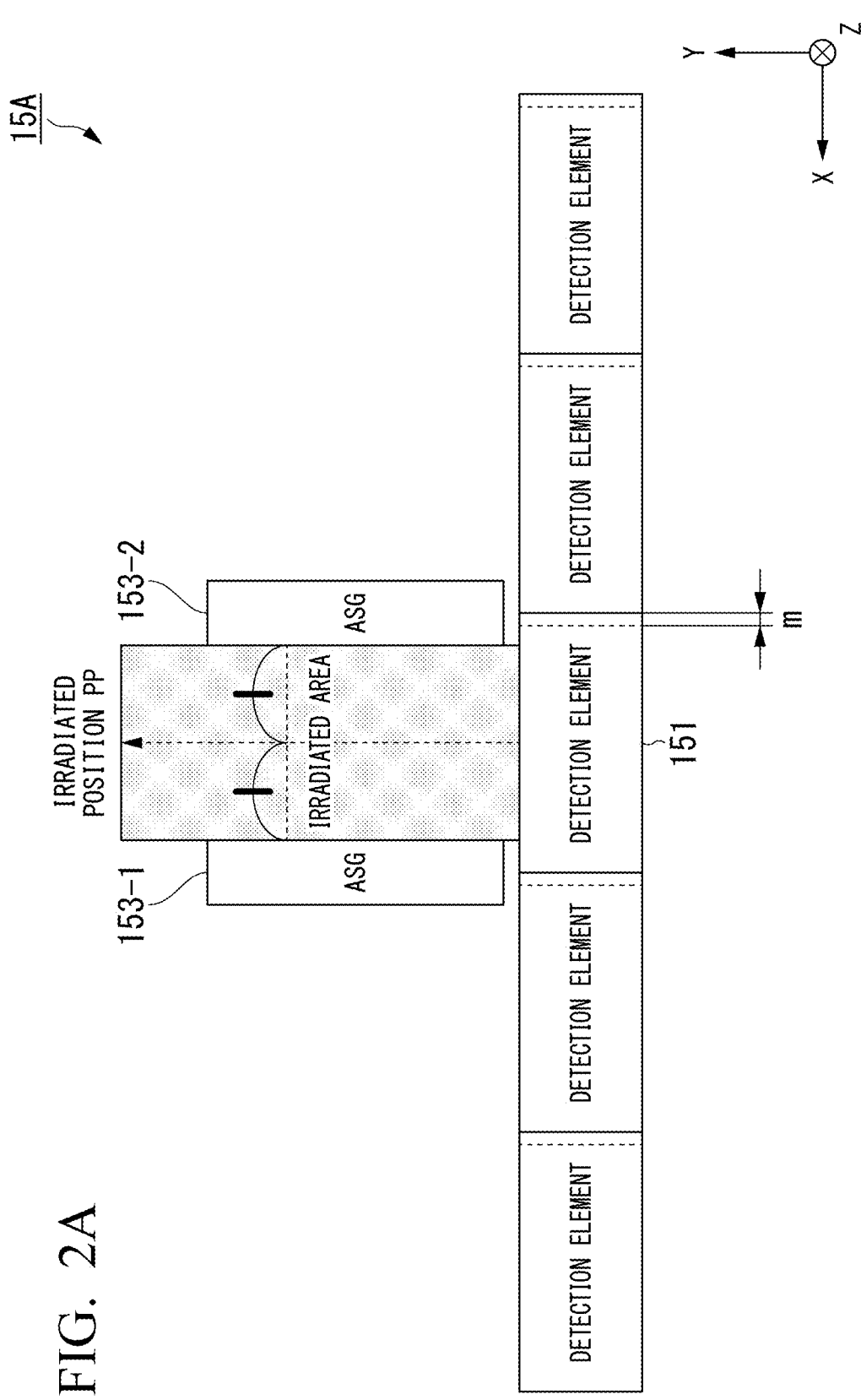
FIG. 2A is a diagram showing the position of the center of gravity of an area to be irradiated with X-rays when one detection element is disposed for one grid of an ASG in an X-ray detector according to a prior art.

FIG. 2A is a diagram showing the position of the center of gravity of an X-ray irradiated area (light receiving area) when one detection element is disposed for one grid of an ASG in an X-ray detector according to the prior art. In the X-ray CT apparatus 1, a CT image is reconstructed by back-projecting a signal that depends on an X-ray flux onto the position of the center of gravity of a range of detection elements that is irradiated with X-rays. FIG. 2A shows an indirect conversion type X-ray detector 15A. In this X-ray detector 15A, a plurality of detection elements 151 are arranged in a channel direction (X-axis direction in FIG. 2A), and one detection element 151 is disposed between adjacent ASG 153-1 and ASG 153-2 corresponding to one grid of an ASG 153. In such a configuration of one grid and one detection element, the area between the adjacent ASG 153-1 and ASG 153-2 becomes an area to be irradiated with X-rays, and the position of the center of gravity therebe-tween is defined as an irradiated position PP (projection position). A case in which the detection element 151 is misaligned with respect to the ASG 153 in this configuration of one grid and one detection element is assumed. In this example, the solid line indicates the assumed position of the designed detection element 151, the dotted line indicates the position of the misaligned actual detection element 151, and the amount of misalignment is m. In this case, since the position of the center of gravity between the ASG 153-1 and the ASG 153-2 is defined as the irradiated position PP, the irradiated position will not be affected as long as a partition wall between the detection elements 151 is hidden in the shadow of the ASG 153 (as long as the partition walls are located below the ASG 153 in the Y-axis direction in FIG. 2A) even if misalignment occurs.

Figure 2B:
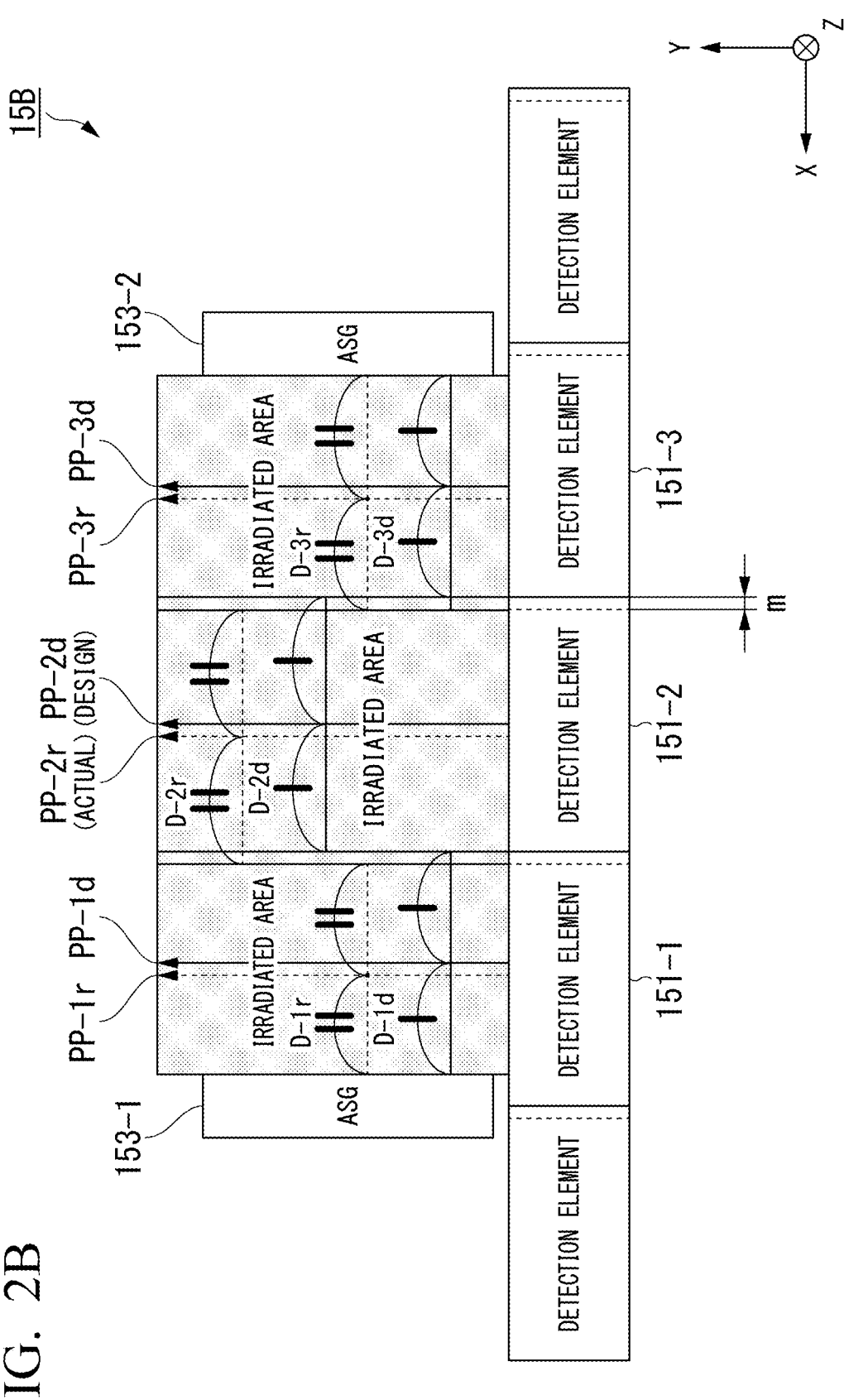
FIG. 2B is a diagram showing the position of the center of gravity of an area to be irradiated with X-rays when a plurality of detection elements are disposed for one grid of an ASG in an X-ray detector according to the first embodiment.

On the other hand, FIG. 2B is a diagram showing the position of the center of gravity of an area to be irradiated with X-rays when a plurality of detection elements are arranged for one grid of ASG in the X-ray detector according to the first embodiment. FIG. 2B shows a direct conversion type X-ray detector 15B. In this X-ray detector 15B, a plurality of detection elements 151 are arranged in the channel direction (X-axis direction in FIG. 2B), and the plurality of detection elements 151 (detection elements 151-1 to 151-3) are arranged between adjacent ASG 153-1 and ASG 153-2 corresponding to one grid of ASG 153. In such a configuration of one grid and a plurality of detection elements, the area between the adjacent ASG 153-1 and ASG 153-2 becomes an area to be irradiated with X-rays. A plurality of detection elements 151 are similarly arranged in the slice direction (Z-axis direction in FIG. 2B). That is, a plurality of ASGs 153 (scattered radiation removal plates) are arranged in parallel at intervals such that two or more of the plurality of detection elements 151 are provided between adjacent ASGs 153 (scattered radiation removal plates) in the channel direction.

In such a configuration of one grid and a plurality of detection elements, with respect to the detection element 151-1 close to the ASG 153-1, the position of the center of gravity between the right end of the ASG 153-1 and the right end of the designed detection element 151-1 is defined as a designed irradiated position PP-1d. The distance along the X-axis from each of the right end of the ASG 153-1 and the right end of the designed detection element 151-1 to the irradiated position PP-1d is a distance D-1d. With respect to the central detection element 151-2, the position of the center of gravity between the left end and the right end of the designed detection element 151-2 is defined as a designed irradiated position PP-2$d$. The distance along the X-axis from each of the left end and the right end of the designed detection element 151-2 to the irradiated position PP-2$d$ is a distance D-2$d$. With respect to the detection element 151-3 close to the ASG 153-2, the position of the center of gravity between the left end of the designed detection element 151-3 and the left end of the ASG 153-2 is defined as a designed irradiated position PP-3$d$. The distance along the X-axis from each of the left end of the designed detection element 151-3 and the left end of the ASG 153-2 to the irradiated position PP-3$d$ is a distance D-3$d$.

A case in which the detection element 151 is misaligned with respect to the ASG 153 in this configuration of one grid and a plurality of detection elements is assumed. In this example, the solid line indicates the assumed position of the designed detection element 151, the dotted line indicates the actual position of the detection element 151 misaligned in the channel direction (X-axis direction in FIG. 2B), and the amount of misalignment is m. When misalignment has occurred in this configuration, the irradiated position is affected. That is, although the detection element 151-1 has the designed irradiated position PP-1$d$, the actual irradiated position PP-lr is the position of the center of gravity between the right end of the ASG 153-1 and the right end of the misaligned actual detection element 151-1. The distance along the X-axis from each of the right end of the ASG 153-1 and the right end of the actual detection element 151-1 to the irradiated position PP-1$r$ is a distance D-lr. Further, although the detection element 151-2 has the designed irradiated position PP-2$d$, the actual irradiated position PP-2$r$ is the position of the center of gravity between the left end and the right end of the misaligned actual detection element 151-2. The distance along the X-axis from each of the left end and the right end of the actual detection element 151-2 to the irradiated position PP-2$r$ is a distance D-2$r$. Further, although the detection element 151-3 has the designed irradiated position PP-3$d$, the actual irradiated position PP-3$r$ is the position of the center of gravity between the left end of the misaligned actual detection element 151-3 and the left end of the ASG 153-2. The distance along the X-axis from each of the left end of the actual detection element 151-3 and the left end of the ASG 153-2 to the irradiated position PP-3$r$ is a distance D-3$r$.

Misalignment of the detection element 151 as described above similarly occurs in the detection elements 151 disposed in the slice direction (Z-axis direction in FIG. 2B) and affects irradiated positions. That is, misalignment may occur between a designed irradiated position and an actual irradiated position.

In the X-ray image diagnostic system of the present embodiment, even if the detection element 151 is misaligned as described above in the configuration of one grid and a plurality of detection elements, the image quality of a generated CT image can be improved by accurately ascertaining the position of the center of gravity of an X-ray receiving area and performing projection processing on the basis of the position of the center of gravity. The present embodiment is also applicable to a sparse channel grid. This makes it possible to simplify the structure and reduce the cost of the X-ray detector.

Referring back to FIG. 1, The DAS 16 collects count data indicating the number of counts of X-ray photons detected by the X-ray detector 15 for a plurality of energy bins, for example, in accordance with a control signal from the control device 18. The count data regarding the plurality of energy bins corresponds to the energy spectrum with respect to X-rays incident on the X-ray detector 15, which has been modified according to response characteristics of the X-ray detector 15. The DAS 16 outputs detection data based on digital signals to the console device 40. The detection data is a digital value of count data identified by the channel number and the row number of a detection element that is a generation source, and a view number indicating a collected view. A view number is a number that changes as the rotary frame 17 rotates, and is a number that is incremented as the rotary frame 17 rotates, for example. Therefore, the view number is information indicating a rotation angle of the X-ray tube 11. A view period is a period that falls between a rotation angle corresponding to a certain view number and a rotation angle corresponding to the next view number. The DAS 16 collects signals output by each of the plurality of detection elements 151. The DAS 16 is an example of a "collector."

The DAS 16 may detect switching of views using a timing signal input from the control device 18, an internal timer, or a signal obtained from a sensor that is not shown. When the X-ray tube 11 is continuously emitting X-rays during full scanning, the DAS 16 collects a group of detection data for the entire circumference (360 degrees). When the X-ray tube 11 is continuously emitting X-rays during half scanning, the DAS 16 collects detection data for half the circumference (180 degrees).

The rotary frame 17 is an annular member that supports the X-ray tube 11, the wedge 12, the collimator 13, and the X-ray detector 15 in a facing manner. The rotary frame 17 is rotatably supported by a fixed frame around the subject P introduced therein. The rotary frame 17 further supports the DAS 16. Detection data output by the DAS 16 is transmitted through optical communication from a transmitter having light emitting diodes (LEDs) provided in the rotary frame 17 to a receiver having photodiodes provided in a non-rotating part (for example, a fixed frame) of the gantry 10 and transferred by the receiver to the console device 40. The method of transmitting the detection data from the rotary frame 17 to the non-rotating part is not limited to the method using optical communication described above, and any non-contact type transmitting method may be employed. The rotary frame 17 is not limited to an annular member and may be an arm-like member as long as it can support and rotate the X-ray tube 11 and the like.

The control device 18 includes, for example, processing circuitry including a processor such as a central processing unit (CPU). The control device 18 receives an input signal from an input interface attached to the console device 40 or the gantry 10 and controls the operations of the gantry 10, the bed device 30, the DAS 16, and the camera 20. For example, the control device 18 rotates the rotary frame 17 or tilts the gantry 10. When tilting the gantry 10, the control device 18 rotates the rotary frame 17 about an axis parallel to the Z-axis direction on the basis of a tilt angle input to the input interface. The control device 18 ascertains the rotation angle of the rotary frame 17 according to the output of a sensor that is not shown, or the like. The control device 18 may be provided on the gantry 10 or may be provided on the console device 40.

The X-ray CT apparatus 1 is, for example, a rotate/rotate-type X-ray CT apparatus (a third generation CT) in which both the X-ray tube 11 and the X-ray detector 15 are supported by the rotary frame 17 and rotate around the subject P, but is not limited thereto and may be a stationary/rotate-type X-ray CT apparatus (a fourth generation CT) in which a plurality of detection elements arranged in an annular shape are fixed to a fixed frame and the X-ray tube 11 rotates around the subject P.

The camera 20 images each detection element included in the X-ray detector 15. The camera 20 is, for example, an infrared camera. The camera 20 radiates infrared light to detection elements, detects the reflected light (reflected light reflected by electrodes provided below the detection elements and the ASG 153), and converts the same into electrical signals. The camera 20 is provided at any position where it can image the detection elements, such as inside the X-ray detector 15. For example, the camera 20 images detection elements inside the X-ray detector 15 from a position substantially normal to a first surface at a time when the X-ray CT apparatus 1 is not performing imaging. The camera 20 may be attachable/detachable to/from the X-ray CT apparatus 1. For example, when the camera 20 is not in use, it may be attached to the bed device 30 and stored.

Figure 3:
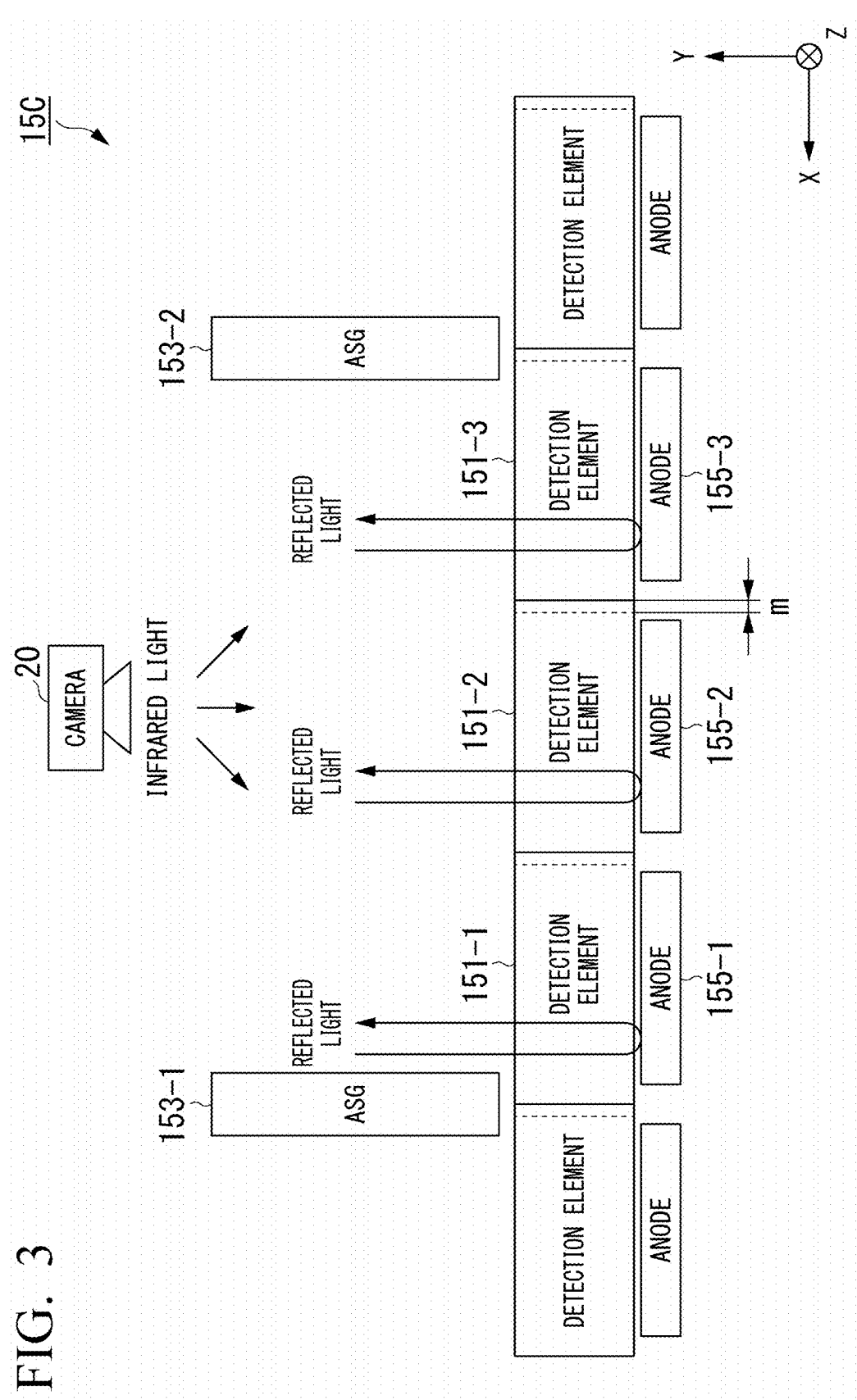
FIG. 3 is a diagram showing a configuration in which data regarding an irradiated area of a detection element is acquired using infrared light (reflected light) according to the first embodiment.

FIG. 3 is a diagram showing a state in which infrared light (reflected light) reflected by a detection element according to the first embodiment is acquired. As shown in FIG. 3, a plurality of detection elements 151 are arranged in the X-ray detector 15C in the channel direction (X-axis direction in FIG. 3). Furthermore, ASGs 153 are similarly arranged in the channel direction (X-axis direction in FIG. 3) on the side of a first surface (X-ray radiation side) of this row of detection elements 151. The X-ray detector 15C has a configuration of one grid and a plurality of detection elements. Anodes 155 are disposed on the side of a second surface of each detection element 151 opposite to the first surface. The camera 20 is provided on side of the first surface and radiates infrared light to the first surface of the detection elements 151. Generally, materials such as cadmium telluride (CdTe), CZT (CdZnTe), and silicon used for the detection elements 151 transmit infrared light. On the other hand, materials such as tungsten (W) and molybdenum (Mo) used for the ASGs 153 and materials such as gold (Au) and platinum (Pt) used for the anodes 155 do not transmit infrared light but reflect it. Therefore, reflected infrared light radiated by the camera 20 captures an image of the anodes 155 and the ASGs 153. Since the ASGs 153 form shadows with respect to infrared light, it is possible to image the detection element 151 (the same area as a field irradiated with X-rays) that is paired with each anode 155 by using the reflected light due to the anode 155. When the detection elements 151 are arranged extending in the body axis direction (row direction, Z-axis direction in FIG. 3), the camera 20 (light source and sensor) is extended in the body axis direction to capture an image of the infrared camera.

Figure 4:
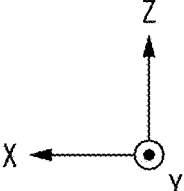
FIG. 4 is a diagram showing an example of a detection element image generated on the basis of infrared light (reflected light) in the first embodiment.

FIG. 4 is a diagram showing an example of a detection element image generated on the basis of infrared light (reflected light) in the first embodiment. As shown in FIG. 4, the detection element image shows an actual X-ray irradiation range of each of a plurality of detection elements 151 (151-1 to 151-9) disposed in the channel direction (X-axis direction in FIG. 4) and the slice direction (Z-axis direction in FIG. 4). By using this detection element image, it is possible to determine the center of gravity C of the actual X-ray irradiation range of each detection element 151.

Referring back to FIG. 1, the bed device 30 is a device on which the subject P to be scanned is placed and moved, and introduced into the rotary frame 17 of the gantry 10. The bed device 30 includes, for example, a base 31, a bed driving device 32, a top plate 33, and a support frame 34. The base 31 includes a housing that supports the support frame 34 such that the support frame 34 can move in the vertical direction (Y-axis direction). The bed driving device 32 includes a motor and an actuator. The bed driving device 32 moves the top plate 33 along the support frame 34 in the longitudinal direction of the top plate 33 (Z-axis direction). Further, the bed driving device 32 moves the top plate 33 in the vertical direction (Y-axis direction). The top plate 33 is a plate-shaped member on which the subject P is placed.

The bed driving device 32 may move not only the top plate 33 but also the support frame 34 in the longitudinal direction of the top plate 33. Further, contrary to the above, the gantry 10 may be movable in the Z-axis direction, and the rotary frame 17 may be controlled to come around the subject P by moving the gantry 10. Further, both the gantry 10 and the top plate 33 may be movable. Further, the X-ray CT apparatus 1 may be an apparatus in which the subject P is scanned in a standing or sitting position. In this case, the X-ray CT apparatus 1 includes a subject support mechanism instead of the bed device 30, and the gantry 10 rotates the rotary frame 17 about an axial direction perpendicular to the floor surface.

The console device 40 includes, for example, a memory 41, a display 42, an input interface 43, a network connection circuit 44, and processing circuitry 50. Although the console device 40 will be described as being separate from the gantry 10 in the present embodiment, the gantry 10 may include some or all of the components of the console device 40.

The memory 41 is realized by, for example, a semiconductor memory element such as a random access memory (RAM) or a flash memory, a hard disk, an optical disc, or the like. The memory 41 stores, for example, design data DD, center of gravity data CD (correction parameters), detection data, projection data, reconstructed image data, information regarding the subject P, imaging conditions, and the like. Such data may be stored in an external memory with which the X-ray CT apparatus 1 can communicate instead of the memory 41 (or in addition to the memory 41). The external memory is controlled by a cloud server that manages the external memory, for example, when the cloud server receives read/write requests.

The display 42 displays various types of information. For example, the display 42 displays a medical image (CT image) generated by the processing circuitry, a graphical user interface (GUI) image for receiving various operations by an operator such as a doctor or a technician, and the like. The display 42 is, for example, a liquid crystal display, a cathode ray tube (CRT), an organic electroluminescence (EL) display, or the like. The display 42 may be provided on the gantry 10. The display 42 may be of a desktop type, or may be a display device (for example, a tablet terminal) that can communicate wirelessly with the main body of the console device 40.

The input interface 43 receives various input operations of an operator, and outputs electrical signals indicating the content of the received input operations to the processing circuitry 50. For example, the input interface 43 receives input operations such as collection conditions at the time of collecting detection data or projection data and reconstruction conditions at the time of reconstructing a CT image. For example, the input interface 43 is realized by a mouse, a keyboard, a touch panel, a track ball, a switch, a button, a joystick, a camera, an infrared sensor, a microphone, etc.

The input interface 43 may be provided in the gantry 10. Further, the input interface 43 may be realized by a display device (for example, a tablet terminal) that can communicate wirelessly with the main body of the console device 40. In this specification, the input interface is not limited to one that includes physical operation parts such as a mouse and a keyboard. For example, examples of the input interface include electrical signal processing circuitry that receives an electrical signal corresponding to an input operation from external input equipment provided separately from the device and outputs this electrical signal to a control circuit.

The network connection circuit 44 includes, for example, a network card having a printed circuit board, a wireless communication module, or the like. The network connection circuit 44 implements an information communication protocol depending on the type of network to be connected.

The processing circuitry 50 controls the overall operation of the X-ray CT apparatus 1, the operation of the gantry 10, the operation of the bed device 30, and the operation of the camera 20. The processing circuitry 50 executes, for example, a system control function 51, a preprocessing function 52, a reconstruction function 53, an image processing function 54, an acquisition function 55, a scan control function 56, a generation function 57, a display control function 58, and the like. These components are realized, for example, by a hardware processor (computer) executing a program (software) stored in the memory 41. The hardware processor is, for example, circuitry such as a CPU, a graphics processing unit (GPU), an application-specific integrated circuit (ASIC), a programmable logic device (for example, a simple programmable logic device (SPLD) or a complex programmable logic device (CPLD), and a field programmable gate array (FPGA)), etc.

The program may be directly incorporated into the circuit of the hardware processor instead of being stored in the memory 41. In this case, the hardware processor realizes the functions by reading and executing the program incorporated into the circuit. The hardware processor is not limited to being configured as a single circuit, but may be configured as one hardware processor by combining a plurality of independent circuits to realize each function. Further, a plurality of components may be integrated into one hardware processor to realize each function.

The components included in the console device 40 or the processing circuitry 50 may be distributed and realized by a plurality of pieces of hardware. The processing circuitry 50 may be realized by a processing device that can communicate with the console device 40 instead of being a component included in the console device 40. The processing device is, for example, a workstation connected to one X-ray CT apparatus, or a device (e.g., a cloud server) that is connected to a plurality of X-ray CT apparatuses and collectively executes the same processing as that performed by the processing circuitry 50 described below.

The system control function 51 controls various functions of the processing circuitry 50 on the basis of input operations received by the input interface 43.

The preprocessing function 52 performs preprocessing such as offset correction processing, inter-channel sensitivity correction processing, and beam hardening correction on detection data output by the DAS 16.

The reconstruction function 53 generates a reconstructed image (CT image) regarding the subject P on the basis of detection data (signal) and data regarding an irradiated area. The reconstruction function 53 includes, for example, a correction function 531. The correction function 531 corrects an irradiated position of detection data on the basis of the data regarding an irradiated area of each detection element generated by the generation function 57. The reconstruction function 53 is an example of a "reconstructor." The reconstruction function 53 generates a reconstructed image by setting the position of the center of gravity of the actual irradiated area of each of the plurality of detection elements 151 included in the data regarding the irradiated area as an irradiated position.

The image processing function 54 converts CT image data into three-dimensional image data or CT image data of an arbitrary cross section using a known method on the basis of an input operation received by the input interface 43. Conversion into three-dimensional image data may be performed by the preprocessing function 52.

The acquisition function 55 acquires an image (detection element image) obtained by imaging the plurality of detection elements 151 that output signals in response to incident X-rays, and a plurality of ASGs 153 (scattered radiation removal plates) arranged at least in the channel direction on the side of the first surface on which X-rays of the plurality of detection elements 151 are incident in a direction substantially normal to the first surface. The acquisition function 55 acquires a detection element image generated on the basis of reflected light data transmitted from the camera 20. The acquisition function 55 includes, for example, an image generation function 551. The image generation function 551 generates a detection element image on the basis of reflected light data. The acquisition function 55 is an example of an "acquirer."

The scan control function 56 controls detection data collection processing in the gantry 10 by instructing the X-ray high voltage device 14, the DAS 16, the control device 18, and the bed driving device 32. The scan control function 56 performs control for monitoring scanning and main scanning. Further, the scan control function 56 controls the operation of each part at the time of capturing for collecting positioning images and capturing images used for diagnosis.

The generation function 57 generates data (center of gravity data) regarding an irradiated area of each of the plurality of detection elements on the basis of the detection element image acquired by the acquisition function 55. The generation function 57 generates data in which information on the position of the center of gravity of the actual irradiated area of each of the plurality of detection elements among the areas of the plurality of detection elements included in the detection element image is set as an irradiated position. The generation function 57 is an example of a "generator." That is, the acquisition function 55 acquires an infrared light image based on output data corresponding to infrared light radiated from a light source provided on the side of the first surface and reflected by an electrode corresponding to each of the plurality of detection elements and a plurality of scattered radiation removal plates, and the generation function 57 generates data regarding irradiated areas on the basis of the infrared light image.

The display control function 58 causes the display 42 to display CT images generated by the processing circuitry, GUI images for receiving various operations performed by operators such as doctors and technicians, detection element images, images showing data regarding irradiated areas, and the like.

According to the above-described configuration, the X-ray CT apparatus 1 scans the subject P in a scanning mode such as helical scanning, conventional scanning, or step-and-shoot. Helical scanning is a mode in which the subject P is scanned in a spiral manner by rotating the rotary frame 17 while moving the top plate 33. Conventional scanning is a mode in which the rotary frame 17 is rotated while the top plate 33 is kept stationary to scan the subject P in a circular orbit. Step-and-shoot is a mode in which the position of the top plate 33 is moved at regular intervals to perform conventional scanning in a plurality of scanning areas.

[Processing Flow]

<Processing of Calculating Center of Gravity Data>

Next, an example of processing of calculating center of gravity data will be described. FIG. 5 is a flowchart showing an example of processing of calculating center of gravity data of a detection element in the X-ray CT apparatus according to the first embodiment. Processing shown in FIG. 5 is started, for example, when an operator of the X-ray CT apparatus 1 issues an instruction to start processing of calculating center of gravity data via the input interface 43 during apparatus maintenance (at the time of assembling or replacing an X-ray detector).

First, the acquisition function 55 transmits an infrared light radiation signal to the camera 20 and causes the camera 20 to radiate infrared light to the detection elements 151 (step S101). The infrared light passes through the detection elements 151, is reflected by the anodes 155 paired with the detection elements 151, and is detected by the camera 20.

Next, the image generation function 551 performs imaging processing on the basis of reflected light data detected by the camera 20 (step S103). Accordingly, a detection element image showing an actual irradiated area of each of the detection elements 151 is generated.

Next, the generation function 57 calculates the position of the center of gravity (coordinates) of the irradiated area of each of the detection elements 151 by performing image analysis on the generated detection element image (step S105). Next, the generation function generates center of gravity data CD in which data regarding the calculated positions of the centers of gravity of irradiated areas of the detection elements 151 is compiled, and stores the center of gravity data CD in the memory 41 (step S107).

Accordingly, processing of this flowchart ends.

<Reconstruction Processing>

Next, an example of reconstruction processing will be described. FIG. 6 is a flowchart showing an example of CT image reconstruction processing in the X-ray CT apparatus according to the first embodiment. Processing shown in FIG. 6 is started, for example, when the operator of the X-ray CT apparatus 1 issues an instruction to start imaging processing of the subject P.

First, the reconstruction function 53 acquires detection data collected by the DAS 16 by irradiating the subject P with X-rays (step S201).

Next, the correction function 531 corrects positions of the centers of gravity defined in advance in design data DD using the data regarding the position of the center of gravity of each of the detection elements 151 included in the center of gravity data CD (step S203).

Next, the reconstruction function 53 reconstructs a CT image of the subject P on the basis of the corrected data regarding the position of the center of gravity (step S205). The reconstructed CT image is displayed on the display 42, for example, and the operator can check the CT image. Accordingly, processing of this flowchart ends.

According to the first embodiment described above, the image quality of an X-ray image can be improved by ascertaining an area to be irradiated with X-rays (actual irradiated range) and accurate irradiated position in a detection element. Since an irradiated position can be accurately determined, the spatial resolution of an X-ray diagnostic apparatus can be improved. Furthermore, artifacts in X-ray images can also be reduced.

Although a configuration example in which one grid is surrounded by four ASGs 153 has been described, the present embodiment is not limited thereto. The present embodiment is also applicable to a configuration in which the ASGs 153 are arranged only in one-dimensional direction (for example, the Z-axis direction in FIG. 7) as shown in FIG. 7.

Second Embodiment

Next, a second embodiment will be described. The second embodiment differs from the first embodiment in that the former targets an indirect conversion type X-ray detector and acquires data regarding an irradiated area of a detection element using transmitted X-ray light. An X-ray CT apparatus 1 of the second embodiment will be described below focusing on differences from the first embodiment.

Figure 8:
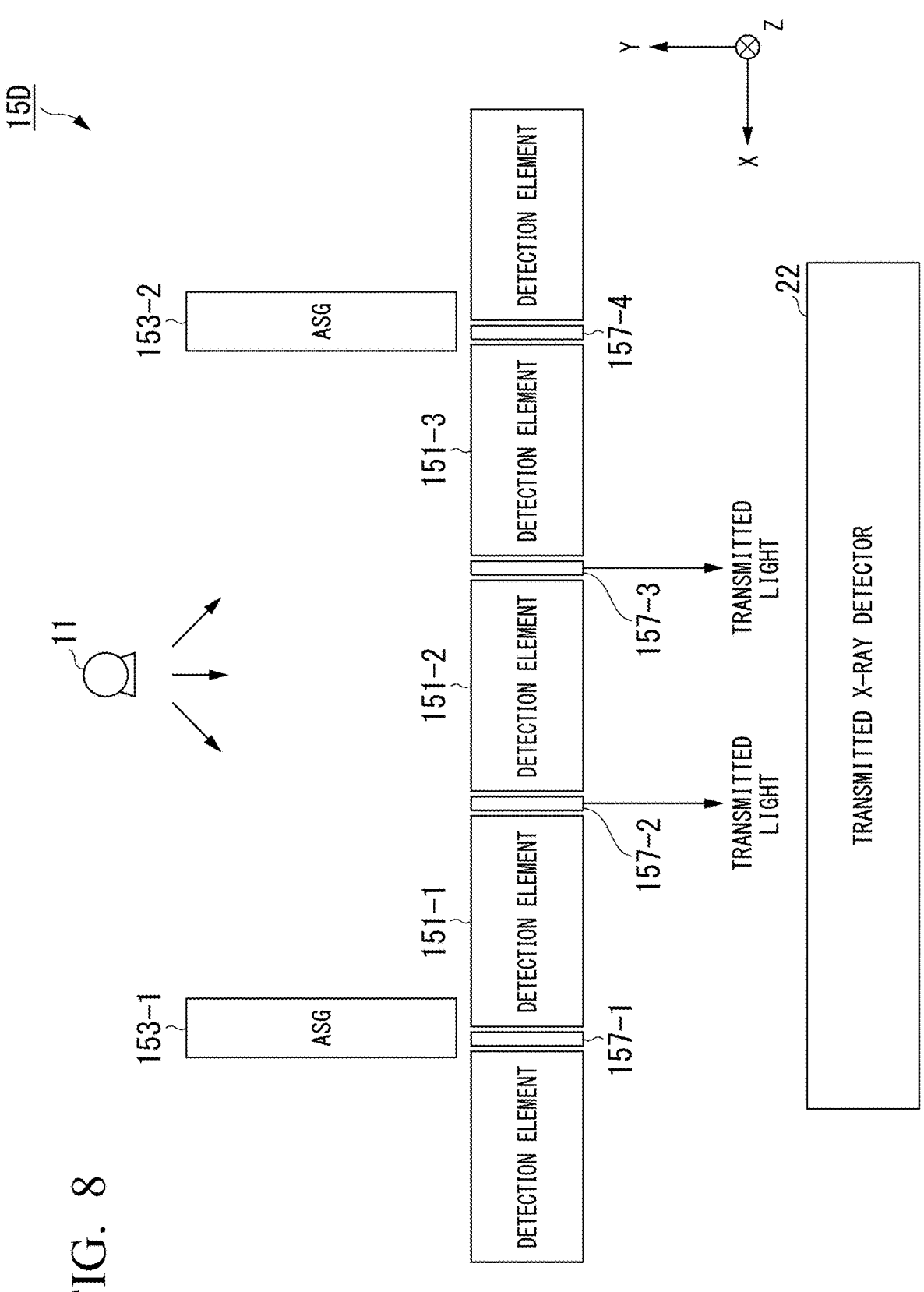
FIG. 8 is a diagram showing a configuration in which data regarding an irradiated area of a detection element is acquired using transmitted X-ray light according to a second embodiment.

FIG. 8 is a diagram showing a configuration in which data regarding irradiated areas of detection elements is acquired using transmitted X-ray light according to the second embodiment. As shown in FIG. 8, a plurality of detection elements 151 are arranged in an X-ray detector 15D in the channel direction (X-axis direction in FIG. 8). Furthermore, ASGs 153 are similarly arranged in the channel direction (X-axis direction in FIG. 8) on the side of the first surface (X-ray radiation side) of the row of the detection elements 151. The X-ray detector 15D has a configuration of one grid and a plurality of detection elements. A partition wall 157 is disposed between the detection elements 151. An X-ray tube 11 is provided on the side of the first surface and irradiates the first surface of the detection element 151 with X-rays. Generally, materials such as GOS, LYSO, CWO, and BGO included in a scintillator used in the indirect conversion type detection elements 151 have high absorption of X-rays. Furthermore, materials used in the ASG 153, such as tungsten (W) and molybdenum (Mo), also have high absorption of X-rays. On the other hand, materials such as epoxy resin and alumina ($Al_2O_3$) used for the partition wall 157 have low absorption of X-rays.

X-rays radiated to the first surface of the detection elements 151 by the X-ray tube 11 are absorbed by the detection elements 151 and the ASGs 153, but transmitted through the partition wall 157 without being absorbed. When an image is generated using detection data obtained by detecting such transmitted X-ray light through a transmitted X-ray detector 22, an image of the partition wall 157 that is not hidden by the ASG 153 is captured. In this image, a shaded area corresponds to the area of the ASG 153 and the detection element 151. Therefore, the image generation function 551 can generate a detection element image of the range of the detection elements 151, that is, an area to be irradiated with X-rays of each detection element 151 by removing the area corresponding to the ASG 153 from the shaded area in this image.

That is, the acquisition function 55 acquires a transmitted image based on output data corresponding to X-rays radiated from the X-ray tube 11 provided on the side of the first surface and transmitted through the partition walls 157 of the plurality of detection elements 151, and the generation function 57 generates data regarding an irradiated area on the basis of the transmitted image. The generation function 57 generates data regarding the irradiated area by excluding the area corresponding to the ASG 153 (scattered radiation removal plate) from a shaded area in the transmitted image.

According to the second embodiment described above, the image quality of an X-ray image can be improved by ascertaining an area to be irradiated with X-rays (actual irradiated area) and accurate irradiated position in a detection element. Since the irradiated position can be accurately ascertained, the spatial resolution of an X-ray diagnostic apparatus can be improved. Furthermore, artifacts in X-ray images can also be reduced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray image diagnostic system comprising processing circuitry configured to:

acquire an image obtained by imaging a plurality of detection elements that output signals in response to incident X-rays, and a plurality of scattered radiation removal plates arranged at least in a channel direction on the side of a first surface of the plurality of detection elements on which the X-rays are incident in a direction substantially normal to the first surface; and generate data regarding an irradiated area of each of the plurality of detection elements on the basis of the image.

2. The X-ray image diagnostic system according to claim 1, wherein the processing circuitry is configured to generate the data in which a position of the center of gravity of an actual irradiated area of each of the plurality of detection elements is set to an irradiated position in areas of the plurality of detection elements included in the image.

3. The X-ray image diagnostic system according to claim 1, wherein the plurality of scattered radiation removal plates are arranged in parallel in the channel direction at intervals to provide two or more of the plurality of detection elements between adjacent scattered radiation removal plates.

4. The X-ray image diagnostic system according to claim 1, further comprising:

the plurality of detection elements;

the plurality of scattered radiation removal plates; and a collector configured to collect signals output by each of the plurality of detection elements, wherein the processing circuitry is configured to generate a reconstructed image on the basis of the signals and the data.

5. The X-ray image diagnostic system according to claim 4, wherein the processing circuitry is configured to generate the reconstructed image by setting the position of the center of gravity of the actual irradiated area of each of the plurality of detection elements included in the data as an irradiated position.

6. The X-ray image diagnostic system according to claim 1, wherein the processing circuitry is configured to:

acquire an infrared light image based on output data corresponding to infrared light radiated from a light source provided on the side of the first surface and reflected by electrodes corresponding to the plurality of detection elements and the plurality of scattered radiation removal plates; and generate the data on the basis of the infrared light image.

7. The X-ray image diagnostic system according to claim 1, wherein the processing circuitry is configured to:

acquire a transmitted image based on output data corresponding to X-rays radiated from an X-ray tube provided on the side of the first surface and transmitted through partition walls of the plurality of detection elements; and generate the data on the basis of the transmitted image.

8. The X-ray image diagnostic system according to claim 7, wherein the processing circuitry is configured to generate the data by excluding an area corresponding to the scattered radiation removal plates from among shaded areas in the transmitted image.

9. An X-ray image diagnostic method, using a computer, comprising:

acquiring an image obtained by imaging a plurality of detection elements that output signals in response to incident X-rays, and a plurality of scattered radiation removal plates arranged at least in a channel direction on a side of a first surface of the plurality of detection elements on which the X-rays are incident in a direction substantially normal to the first surface; and generating data regarding an irradiated area of each of the plurality of detection elements on the basis of the image.

10. A computer-readable non-transitory storage medium storing a program causing a computer to:

acquire an image obtained by imaging a plurality of detection elements that output signals in response to incident X-rays, and a plurality of scattered radiation removal plates arranged at least in a channel direction on a side of a first surface of the plurality of detection elements on which the X-rays are incident in a direction substantially normal to the first surface; and generate data regarding an irradiated area of each of the plurality of detection elements on the basis of the image.

* * * * *